United States Patent [19]

Singer et al.

[11] Patent Number: 5,070,455
[45] Date of Patent: Dec. 3, 1991

[54] IMAGING SYSTEM AND METHOD USING SCATTERED AND DIFFUSED RADIATION

[75] Inventors: Jerome R. Singer; Francisco A. Grunbaum, both of Berkeley; Philip D. Kohn, Oakland; Jorge P. Zubelli, Berkeley; John L. Couch, San Francisco, all of Calif.; Harold L. Naparst, Sommerville, Mass.; Geoffrey Latham, Braddon, Australia

[73] Assignee: Singer Imaging, Inc., Berkeley, Calif.

[21] Appl. No.: 440,088

[22] Filed: Nov. 22, 1989

[51] Int. Cl.⁵ .............................................. G06F 15/00
[52] U.S. Cl. ............................................... 364/413.19
[58] Field of Search ....................... 364/413.19, 413.14

[56] References Cited

U.S. PATENT DOCUMENTS

| | | | |
|---|---|---|---|
| 3,778,614 | 12/1973 | Hounsfield | 364/413.14 |
| 4,337,799 | 7/1982 | Abele et al. | 364/413.19 |
| 4,422,146 | 12/1983 | Yamaguchi et al. | 364/413.19 |
| 4,850,002 | 7/1989 | Harding et al. | 378/87 |

OTHER PUBLICATIONS

"Image Reconstruction of the Interior of Bodies That Diffuse Radiation", J. R. Singer et al., SCIENCE, vol. 248, pp. 990-993 (May 25, 1990).
"Early Two-Dimensional Reconstruction and Recent Topics Stemming From It", A. M. Cormack, Science, vol. 209, pp. 1482-1486 (1980).
"Computed Medical Imaging", G. N. Hounsfield, SCIENCE, vol. 210, pp. 22-28, (Oct. 3, 1980).

Primary Examiner—Clark A. Jablon
Assistant Examiner—Laura Brutman
Attorney, Agent, or Firm—Flehr, Hohbach, Test, Albritton & Herbert

[57] ABSTRACT

An imaging system generates images of the interior of an object using radiation which is attenuated and scattered by the interior of the object. The object is radiated at a number of points near the exterior of the object, and the radiation emerging from the object is measured at an array of exit points near the exterior of the object. The interior of the object is modelled as an array of volume elements called voxels. Each voxel is modelled as having scattering and attenuation properties, represented by numerical coefficients. The system computes the intensity of radiation that would emerge from the object at the exit points if the interior of the object were characterized by a currently assigned set of values for the scattering and attenuation coefficients. Then, the differences between the measured intensities and the computer intensities are used to compute an error function relates to the magnitude of the errors in the reconstruction. This error function is then minimized using a gradient descent methodology, i.e., the value of the coefficients are modified so as to reduce the value of the error function. The coefficients are repeatedly updated in this manner until the error function falls below a specified threshold value. The final values of the scattering and attenuation coefficients from this process are mapped so as to generate a series of images of the interior of the object depicting the attenuation and scattering characteristcs of the object's interior.

16 Claims, 8 Drawing Sheets

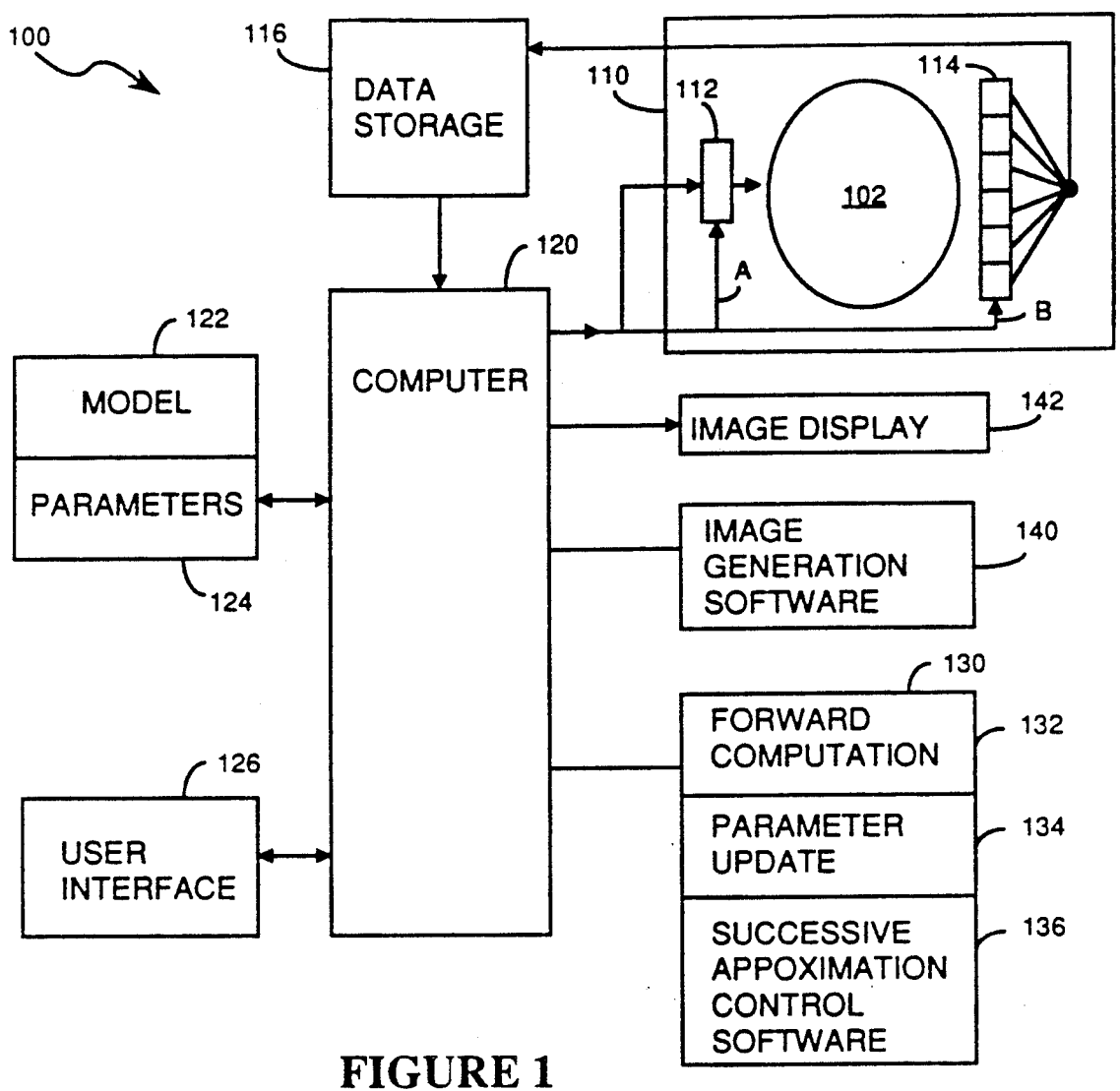
FIGURE 1
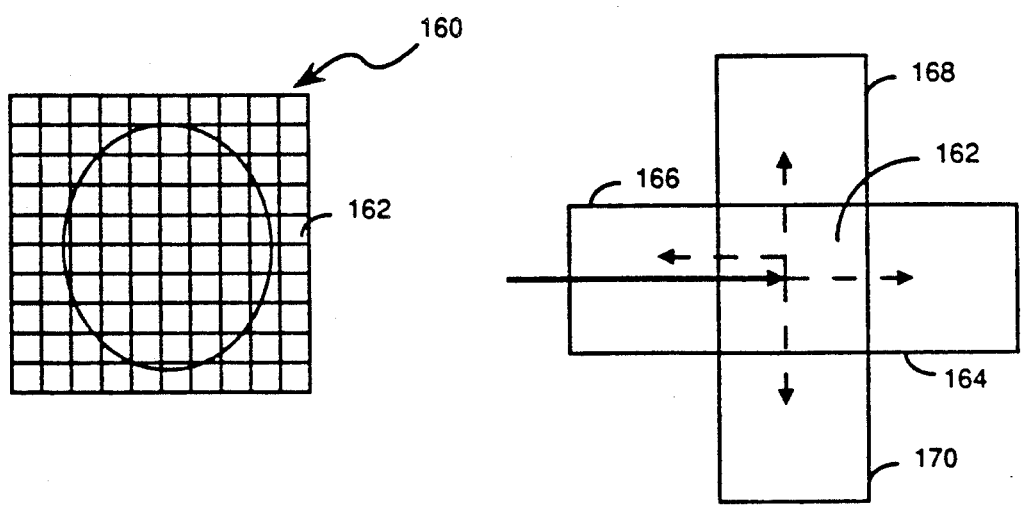
FIGURE 2
FIGURE 3

IMAGING SYSTEM AND METHOD USING SCATTERED AND DIFFUSED RADIATION

The present invention relates generally to systems which produce images of the interior of an object and particularly to methods and systems for imaging the interior of an object using scattered radiation or scattered particles.

BACKGROUND OF THE INVENTION

Most systems which produce images of the interior of an object, such as the human body, utilize in-line unscattered radiation, such as x-ray sources and detectors. These systems measure, for the most part, unscattered radiation and use those measurements as the input data in a mathematical procedure of reconstructing images of the x-rayed object. The measurements in x-ray imaging systems correspond only to the relative loss of straight-through radiation as it passes through the body that is being imaged. It may be noted that magnetic resonance imaging uses an entirely different data collection and image reconstruction technique which is not related to the present invention.

Unlike the prior art, the present invention uses radiation, such as photons, phonons, neutrons or other particles, which will be scattered to a significant degree by the internal structures in various objects. The present invention radiates an object and measures the attenuated and scattered radiation at a number of points along the exterior of the object. The inventors have found that these measurements are sufficient to determine the scattering and attenuation properties of the various regions inside the object.

In the following description, since the invention can be implemented using a number of different types of radiation sources, we utilize the term "light" to represent whichever particle or type of radiation is being employed, whether it be infrared light, visible light, phonons, neutrons or other particles.

In accordance with the present invention, the interior of the object is modelled as an array of volume elements, herein called voxels. Each voxel in the model of the object has scattering and attenuation properties which are represented by numerical parameters that can be mapped so as to generate several images of the interior of the object.

It is believed by the inventors that the technique of the present invention has not been tried in the past because it has been assumed, at least implicitly, that the scattered light exiting an object would simply not contain sufficient information to generate an image of the interior of that object. For instance, any one photon travelling through the object may be scattered multiple times. In addition, photons travelling on a number of different paths can emerge at the same point on the exterior of the body. Thus, it would appear that the amount of light exiting an object at an array of points along the outside of the object would not contain sufficient information to uniquely identify the scattering and attenuation properties of the object's interior. However, the inventors have made the surprising discovery that there is, in fact, more than sufficient information to determine the internal properties of the object.

SUMMARY OF THE INVENTION

In summary, the present invention is a system for generating an image of the interior of an object using radiation which is scattered and attenuated by the interior of the object. The imaging system includes a subsystem for sequentially radiating an object with light from an array of entry points near the exterior of the object, and for measuring the intensity of light emerging from the object at exit points near the exterior of the object each time that the object is radiated with light at a different entry point.

The interior of the object is modelled as an array of volume elements, herein called voxels. Each voxel in the model of the object has scattering and attenuation properties which are represented by numerical coefficients that can be mapped so as to generate several images of the interior of the object. After collecting the imaging data, the scattering and attenuation coefficients for all the voxels are assigned initial values, which helps to shorten the computation process.

Next, the system computes the intensity of light that would emerge from the object at the exit points if the interior of the object were characterized by the currently assigned values for the scattering and attenuation coefficients. Then, the differences between the measured light intensities and the computed light intensities are used to compute an error function related to the magnitude of the errors in the reconstruction. This "error" or "cost" function is then minimized using a gradient descent methodology, i.e., the value of the coefficients are modified so as to reduce the value of the error function.

The process of computing exiting light intensities based on the currently assigned values for the scattering and attenuation coefficients and then comparing the differences between the computed values and the measured values to generate a new approximation of the scattering and attenuation properties of the object continues until the error function (which corresponds to the differences between the measured and computed exiting light intensities) falls below a specified threshold value. The final values of the scattering and attenuation coefficients from this process are then mapped so as to generate a series of images of the interior of the object depicting the attenuation and scattering characteristics of the object's interior.

BRIEF DESCRIPTION OF THE DRAWINGS

Additional objects and features of the invention will be more readily apparent from the following detailed description and appended claims when taken in conjunction with the drawings; in which:

FIG. 1 is a block diagram of an imaging system in accordance with the present invention.

FIG. 2 schematically depicts how an object is modelled as an array of volume elements.

FIG. 3 schematically depicts the attenuation, scattering and reflection properties of a single volume element.

DESCRIPTION OF THE PREFERRED EMBODIMENT

Figure 4:
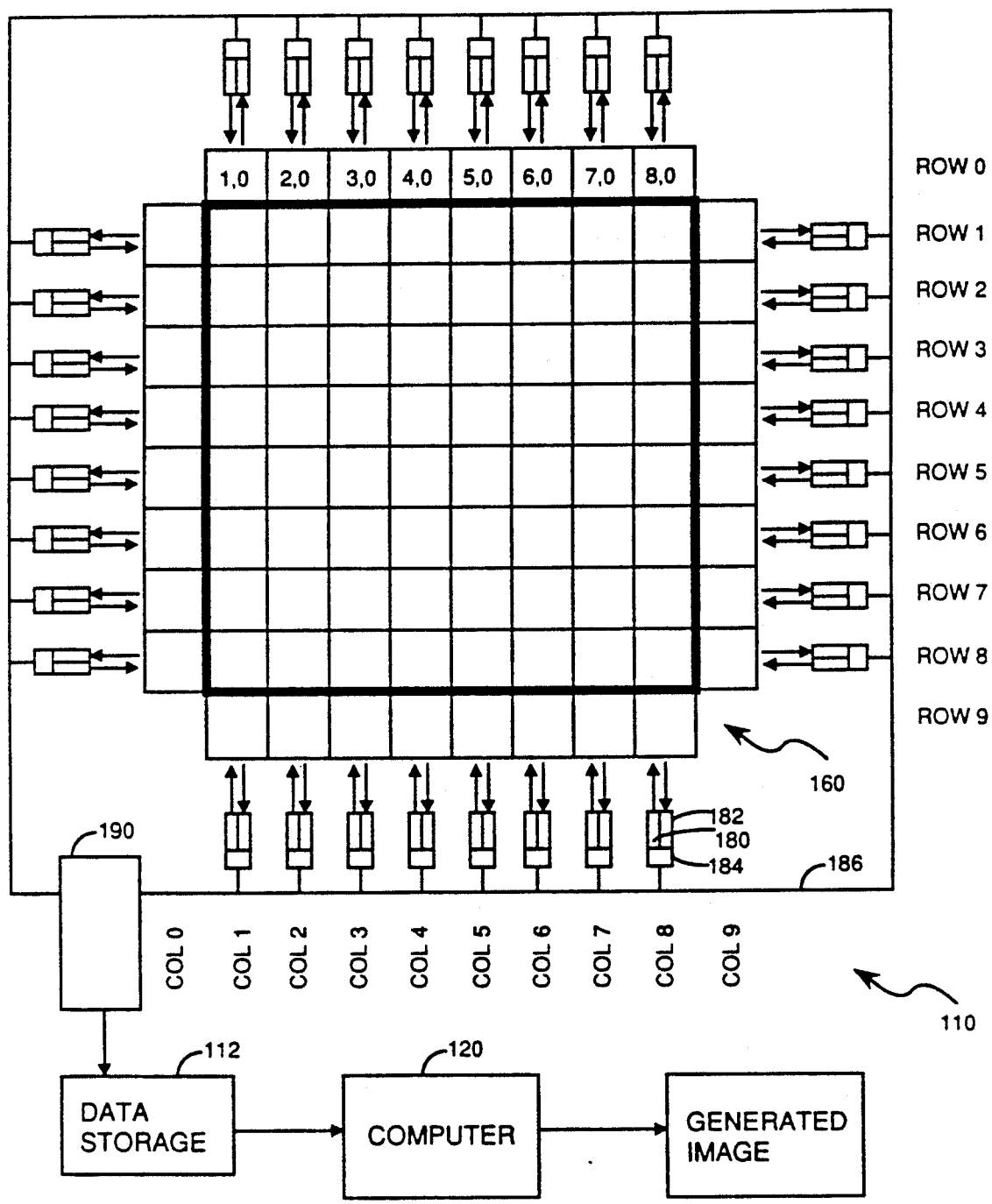
FIG. 4 is a block diagram of a measurement subsystem in accordance with the present invention.

Referring to FIG. 1, there is shown an imaging system 100 which generates an image of the internal structure of an object 102 based on measurements of scattered radiation which passes through the object.

A measurement subsystem 110 radiates the object 102 with radiation, such as visible or infrared light, which will be scattered to a significant degree by the internal structures in the object. The measurement subsystem 110 includes a radiator system 112 (e.g., a particle radiator or a lighting system) for sequentially radiating an object with light from an array of entry points near the exterior of the object, and a sensor system 114 (e.g., an array of particle detectors or light sensors) for measuring the intensity of light emerging from the object at array exit points near the exterior of the object each time that the object is radiated with light at a different entry point. The measurement data generated by the measurement subsystem 110 is stored in a data storage device 116 and processed by a digital computer 120. Furthermore, the computer 120 generates positioning control signals A and B for controlling the set of positions of the radiation source(s) 112 and detectors 114, respectively, so as to obtain data sets sufficient for reconstructing an image of the interior structure of the object 102.

A software model 122 is used to represent the interior of the object as an array of volume elements, called voxels. In accordance with this model 122, the interior of the object 122 is modelled by a set of numerical parameters 124 which include scattering and attenuation coefficients for each of the voxels. These coefficients are assigned initial values by either the model 122, or by a user via the user interface 126. The model 122 in the preferred embodiment initializes the coefficients in all the voxels with the same set of values, which corresponds to an object with a totally uniform interior. However, the user may want to speed the imaging process by providing initial coefficient values based on what the user expects to find in the interior of the object.

The parameters 124 used to model the interior of the object 102 are processed by the computer 120 under the control of a set of software 130 which has three major components. A "forward computation" module 132 computes the intensity of light that would emerge from the object at the exit points if the interior of the object were characterized by the currently assigned values for the scattering and attenuation coefficients.

A parameter updating module 134 computes updated parameter values based on the differences between the measured light intensities and the computed light intensities. More particularly, it first computes an error function which is equal to the sum of the squares of the differences between the measured light intensities and the computed light intensities.

$$\text{ERROR\_FCN} = \sum_{i=1}^{4N} (\text{Measured Intensity at Sensor } i - \text{Computed Intensity at Sensor } i)^2$$

It then computes a multi-dimensional slope or gradient of this error function. This multi-dimensional gradient is vector, the components of which are the partial derivatives of the error function with respect to each of the parameter values:

$$\text{gradient} = (\text{grad}(p_1), \text{grad}(p_2), \ldots \text{grad}(p_{3N2}))$$

$$\text{grad}(p_i) = \frac{\partial}{\partial p_i} (\text{ERROR\_FCN})$$

where ERROR_FCN is the error function and grad($p_i$) is the partial derivative of the error function with respect to parameter $p_i$.

Next, the parameter updating module generates new values for the parameters by adjusting the current values of the parameters in a direction opposite to the gradient of the error function. That is, each individual parameter is adjusted in a way that is related to the multi-dimensional slope and the differences between the computed and measured intensity values:

$$p(x)_{i+1} = p(x)_i - f(\text{ERROR\_FCN}, \text{gradient}, x)$$

where $p(x)_i$ is the current value of one individual parameter, $p(x)_{i+1}$ is the adjusted value of that parameter, and f(ERROR_FCN,gradient,j) is a computed adjustment factor that is a function of the error function ERROR_FCN, the gradient of the error function ERROR_FCN, and the parameter p(x) that is being modified.

A successive approximation control software module 136 makes repeated calls to the forward computation and parameter update modules 132 and 134 until the value of the error function falls below a specified threshold value. The final values of the scattering and attenuation coefficients from this process are then mapped by image generation software 140 so as to generate an image of the interior of the object which is displayed or printed by an image display device 142.

Referring to FIG. 2, there is shown a two dimensional example of how the interior of an object is modelled as an array 160 of volume elements. Each volume element 162 encloses a rectangular or cube-shaped portion of the area inside the measurement subsystem 110.

Referring to FIG. 3, each voxel is modeled as having a set of light transmitting characteristics. In particular, it is assumed that the light transmitting characteristics of each voxel can be represented by an attenuation coefficient, and a set of three scattering coefficients: a forward scattering coefficient, a backward scattering coefficient, and a sideways scattering coefficient. As photons travel through each voxel inside the object, they are subject to attenuation and scattering. Attenuation is the process by which the radiation being used for imaging is absorbed by the object. For instance, photons are converted into other forms of energy and thus are absorbed by the object. Scattering is the process by which the radiated particles (e.g., photons) that are not absorbed are deflected from a straight path.

The attenuation coefficient for a voxel represents the probability that a radiated particle (photon) which arrives at the voxel will not emerge from it. The backwards scattering coefficient for a voxel represents the probability that a radiated particle (photon) which emerges from the voxel will be reflected back to the voxel from which it arrived. The sideways scattering coefficient for a voxel represents the probability that a radiated particle (photon) emerging from the voxel will have been deflected from a straight path though the voxel to a neighboring voxel. Finally, the forward scattering coefficient of a voxel represents the probability that a radiated particle (photon) that emerges from the voxel will keep moving in the direction that it entered the voxel.

If one were to use radiation such as X-rays, gamma rays, or other particles which provide good transmission through the object, one could minimize the effect of scattering and thus reconstruct two or three dimensional maps of the attenuation characteristics of the object. That is the methodology used in standard x-ray tomographic reconstruction, which is a well defined and well understood technology. In the limiting case, when back scattering and side scattering are so small that they can be ignored, the present invention becomes equivalent to standard x-ray tomographic reconstruction.

The present invention can utilize much lower radiation energies than that used in x-ray systems. As a result, the present invention can be used in situations where the amount of energy deposited in a patient or other object is of primary concern, as well as in other routine clinical procedures.

Energy deposited on the object at one point of the periphery by a collimated beam of photons will not, in general, exit on the opposite side of the object because a certain amount of attenuation and scattering will occur as photons travel through the object. Instead, the path followed by the photons in the collimated beam will depend on the internal properties of the object that is being imaged and will not be known a priori. If one conceives of the object as a collection of small volume units or voxels as shown in FIG. 2, a photon will travel from voxel to voxel. At each voxel 162 the photon may travel forward to voxel 164, be reflected to voxel 166, or scattered sideways to a neighboring voxel 168 or 170, with this process continuing until the photon is either absorbed or emerges from the object and is detected by a sensor in the measurement subsystem.

Referring to FIG. 4, there is shown a somewhat more detailed block diagram of the measurement subsystem 110. In this example, a two dimensional slice through the object (not shown) is modelled as having an 8x8 array 160 of voxels. As shown, the size of each voxel corresponds to the distance between adjacent sensors points in the system's array of light sensors.

There is a collimated beam generator 180 (also called a light source) and a light sensor 182 located at both ends of each row and column of the array 160. Each generator-sensor pair is coupled by an addressable interface 184 and a communications bus 186 to the measurement subsystem's controller 190. Controller 190 sequentially activates the collimated beam generators 180 one at a time, reads the measurement values from the sensors 182, and stores the measurement values in data storage module 116. In this example, since there are thirty-two light sources 180 and sensors 182, there will be thirty-two sets of measurements, each containing thirty-two measurement values.

Computation Method

It should be noted that the methodology of the present invention will be described primarily for a two dimensional imaging system. This is done only for ease of exposition. The methodology of the present invention is equally applicable to a three dimensional imaging system, although it requires more computations because of the increased number of measurements and the increased number of parameters to be computed. In fact, only the three dimensional case is physically correct, since the scattering process inevitably scatters many particles outside the imaging plane in a two dimensional imaging system, thereby rendering the two dimensional picture inadequate.

As shown in FIG. 4, the object is divided into an N by N array of volume elements, called pixels or voxels. A parameter associated with a particular voxel will be denoted as $X_{ij}$, with indices i and j having values between 1 and N. Each voxel in the model of the object is modelled as having an attenuation coefficient $V_{ij}$, and scattering coefficients $f_{ij}$, $b_{ij}$ and $s_{ij}$. $w_{ij}$, which is equal to $1 - V_{ij}$, is the probability that a photon will not be absorbed by the voxel. $w_{ij}f_{ij}$ is the probability that a photon entering the voxel will be transmitted through the voxel in the same direction that it entered the voxel. $w_{ij}b_{ij}$ is the probability that a photon will be reflected by the voxel back to the voxel from whence it came. $w_{ij}s_{ij}$ is the probability that a photon entering the voxel will be scattered to the side. The relative values of the scattering coefficients are governed by the equation $$f_{ij} + b_{ij} + 2 * s_{ij} = 1 \qquad \text{(Eq. 1)}$$

for a two dimensional imaging system. For a three dimensional imaging system the scattering coefficients are governed by the equation $$f_{ij} + b_{ij} + 4 * s_{ij} = 1 \qquad \text{(Eq. 2)}$$

These coefficients comprise a model for the "photon dynamics" of a voxel, i.e., the microscopic process by which a photon enters and leaves a given voxel. These coefficients are given in terms which are, for the most part, not directly available for measurement.

The present invention provides a mechanism for relating these internal voxel coefficients to a set of "exit probabilities" which correspond to light intensities that can be measured by the light sensors outside the object.

The basis for our model is a "two step Markov transition mechanism". That is, we assume that the transition mechanism of a photon that is at voxel position (i,j) depends only on its present and immediately previous position, and not on its previous history. Given the previous position of a photon, we can say that a photon is at position (i,j), having arrived from the up(u), down(d), right(r) or left(l) directions.

For a given detector position (x,y) we will derive equations for the quantities:

$P_{ij}^u$, $P_{ij}^d$, $P_{ij}^r$, and $P_{ij}^l$  $1 \leq i, j \leq N$ where the superscripts u, d, r and l denote photons entering voxel (i,j) from the up, down, right and left positions, respectively.

These quantities $P_{ij}^*$ (where the asterisk stands for u, d, r and l) stand for the probabilities that a photon that has started from voxels (i,j), having arrived from one of its four neighbors, would exit the object at a specified one of the detectors outside the object. For an object modelled by an N×N array of voxels, there are $4N^2$ such quantities for each specified detector.

It is important to remember that each quantity $P_{ij}^*$ corresponds to a particular detector position, even though our notation for these probability quantities $P_{ij}^*$ does not denote the detector position. If detector positions were given by (x,y) the probability quantities could be denoted as $P_{ij}^*(x,y)$.

It should also be noted that most of these probability values $P_{ij}^*$ cannot be directly measured, since we only inject photons at the boundary of the object and thus can measure only the ones that correspond to voxels on the border of the object, namely:

$P_{li}^u$ for the top border
$P_{iN}^r$ for the right border
$P_{Ni}^d$ for the lower border
$P_{il}^l$ for the left border Of the total $4N^2$ such quantities that we have introduced for each light sensor, we can directly measure only the 4N quantities noted above. We will refer to these 4N quantities as "external" or "source" variables.

In addition, for reasons that will be clear from the following analysis, we augment the N×N array of voxels with two rows and two columns of N voxels at locations 0,1 through 0,N: for the top border
1,N+1 through N,N+1: for the right border
N+1,1 through N+1,N: for the bottom border
1,0 through N,0: for the left border as shown in FIG. 4. In conjunction with these 4N extra voxels, we have 4N quantities denoted as $P_{ij}^*$ for the values of the indices (i,j) listed above. These variables, herein called "detector" variables, will serve as "markers" that indicate the detector for which the probability values are being computed.

For the top border we will give values to $P_{0,j}^d$, for the right border to $P_{i,N+1}^l$, for the left border to $P_{i,0}^r$, and for the bottom border we will give values to $P_{N+1,j}^u$. If the detector in question is, say, at location (0,3), we assign to $P_{0,3}^d$ the value 1, and we assign the value 0 to all the other 4N−1 detector variables. Thus these variables serve as markers to indicate which detector is active.

The remaining $P_{ij}^*$ variables, for i or j equal to 0 or N+1 do not enter into the equations shown below and therefore need not be assigned any values.

The basic matrix equation relating the probability variables to the attenuation and scattering coefficients is as follows:

$$\begin{bmatrix} P_{ij}^u \\ P_{ij}^d \\ P_{ij}^r \\ P_{ij}^l \end{bmatrix} = w_{ij} \begin{bmatrix} f_{ij}b_{ij}s_{ij}s_{ij} \\ b_{ij}f_{ij}s_{ij}s_{ij} \\ s_{ij}s_{ij}f_{ij}b_{ij} \\ s_{ij}s_{ij}b_{ij}f_{ij} \end{bmatrix} \begin{bmatrix} P_{i+1,j}^u \\ P_{i-1,j}^u \\ P_{i,j-1}^r \\ P_{i,j+1}^l \end{bmatrix} \quad \text{(Eq. 3)}$$

Note that there are one of the above matrix equations for each of the $N^2$ voxels. Each of these matrix equations is really four scalar equations. Thus, for a single selected detector we have $4N^2$ equations. Since there are 4N detectors, we will have a total of $4N * 4N^2 = 16N^3$ equations.

As an example, the following are the equations, as defined by the above matrix equation, for voxels (i=1,j=3) and (i=1,j=2) for a detector at position (0,3).

$$P_{13}^u = w_{13}(f_{13}{}^*P_{23}^u + b_{13}{}^*1 + s_{13}{}^*P_{12}^r + s_{13}{}^*P_{14}^l)$$

$$P_{13}^d = w_{13}(b_{13}{}^*P_{23}^u + f_{13}{}^*1 + s_{13}{}^*P_{12}^r + s_{13}{}^*P_{14}^l)$$

$$P_{13}^r = w_{13}(s_{13}{}^*P_{23}^u + s_{13}{}^*1 + f_{13}{}^*P_{12}^r + b_{13}{}^*P_{14}^l)$$

$$P_{13}^l = w_{13}(s_{13}{}^*P_{23}^u + s_{13}{}^*1 + b_{13}{}^*P_{12}^r + f_{13}{}^*P_{14}^l)$$

$$P_{12}^u = w_{12}(f_{12}{}^*P_{22}^u + b_{12}{}^*0 + s_{12}{}^*P_{11}^r + s_{12}{}^*P_{13}^l)$$

$$P_{12}^d = w_{12}(b_{12}{}^*P_{22}^u + f_{12}{}^*0 + s_{12}{}^*P_{11}^r + s_{12}{}^*P_{13}^l)$$

$$P_{12}^r = w_{12}(s_{12}{}^*P_{22}^u + s_{12}{}^*0 + f_{12}{}^*P_{11}^r + b_{12}{}^*P_{13}^l)$$

$$P_{12}^l = w_{12}(s_{12}{}^*P_{22}^u + s_{12}{}^*0 + b_{12}{}^*P_{11}^r + f_{12}{}^*P_{13}^l)$$

Note that in the above equations for a detector at position (0,3), $P_{03}^d$ equals 1 and $P_{02}^d$ equals 0.

The set of $4N^2$ variables $P_{ij}^*$, for values of i and j in the range $1 \leq i,j \leq N$, includes 4N external variables:

$$P_{li}^u, P_{iN}^r, P_{Ni}^d, P_{il}^l \text{ for } 1 \leq i,j \leq N \quad \text{(Eq. 4)}$$

with the remaining $4N^2 - 4N$ variables $P_{ij}^*$ being called "internal" variables.

We now define three vectors X, Y, and Z as follows. X is a vector consisting of the 4N detector variables as defined above. Y is a vector consisting of the 4N external variables, and Z is a vector consisting of the $4N^2 - 4N$ internal variables.

Next, recalling that there are $4N^2$ equations associated with each detector, we write those $4N^2$ equations in matrix form as follows:

Rows: (Eq. 5)

$$\begin{array}{c} 4N \\ 4N^2 - 4N \end{array} \begin{bmatrix} I & C & D \\ 0 & A & B \end{bmatrix} \begin{bmatrix} Y \\ Z \\ X \end{bmatrix} = \begin{bmatrix} 0 \\ 0 \end{bmatrix}$$

Columns: $4N$ $4N^2 - 4N$ $4N$        1         1 where I is the identity matrix, C is a matrix having 4N rows and $4N^2 - 4N$ columns, D is a 4N by 4N matrix, A is a square matrix having $4N^2 - 4N$ rows and $4N^2 - 4N$ columns, and B is a matrix having $4N^2 - 4N$ rows and 4N columns.

In addition, recall that selecting one detector amounts to setting one of the components of the detector variables in the X vector equal to 1, and setting all the other detector variables in the X vector to 0. Thus there will be 4N such sets of equations, one for each of the 4N detectors.

An equivalent representation of the above matrix equation is as follows:

$$Y + CZ + DX = 0 \quad \text{(Eq.6)}$$

$$AZ + BX = 0 \quad \text{(Eq.7)}$$

Matrix D is a square matrix which relates each of the external variables to a corresponding one of the detector variables. Therefore all of the diagonal elements of the D matrix are equal to $w_{ij}b_{ij}$, where $w_{ij}$ and $b_{ij}$ are the attenuation and backward scattering coefficients for the corresponding voxels. In addition, for each voxel located at a convex corner of the object being imaged, there is one off-diagonal element in the D matrix with a nonzero value. All the other elements of the D matrix are equal to zero.

The C matrix specifies the relationship between each external variable and the internal variables. At most, three elements in each row of matrix C will have a nonzero value. To understand this, remember that each variable can be expressed as a weighted combination of four other variables, corresponding to the four neighboring voxels. Looking at FIG. 4, it can be seen that in the case of an external variable for a particular voxel on the periphery of the object being imaged, the equation for the variable will involve one detector variable, and three internal variables if the voxel is not on a "corner" of the object. For the few voxels located on a corner, the equation for the external variable contains only two internal variables, and two detector variables (at least one of which will have a value of zero). Therefore the rows of the C matrix for non-corner external variables have three nonzero elements and the rows of the C matrix for corner external variables have two nonzero elements.

Matrix A is similar to matrix C, except that it is used to relate each internal variable to other ones of the internal variables. Therefore all the diagonal elements of matrix A will be equal to 1 and each row will have at most four nonzero off-diagonal elements, namely $$-w_{ij}f_{ij}, -w_{ij}b_{ij}, -w_{ij}s_{ij}, -w_{ij}s_{ij}.$$

Since the sum of these of-diagonal elements is $-w_{ij}$, and $0 \leq w_{ij} \leq 1$, we have a diagonally dominant matrix. If we can impose the physically reasonable restriction $w_{ij} < 1$, matrix A is strictly diagonally dominant. In this case the, matrix A is invertible.

Matrix B has rows with nonzero elements only for rows corresponding to voxels along the periphery of the object being imaged. For those voxels, two elements per row may have a nonzero value for voxels on convex corners of the object, and only one element per row may have a nonzero value for other voxels on the periphery of the object.

By inverting the A matrix, the above matrix equations (Eq. 6 and Eq.7) can be rewritten as follows:

$$Z = -A^{-1}BX \quad \text{(Eq.8)}$$

$$Y = -CZ - DX = (CA^{-1}B - D)X \quad \text{(Eq.9)}$$

The Forward Solution

The term "the forward solution" refers to the following scenario: if we know the values of $w_{ij}$, $f_{ij}$, $b_{ij}$ and $s_{ij}$ for all the voxels in the object, and we shine a known amount of light at a specified voxel on the periphery of the object, we can compute the amount of light that will be detected by each of the detectors around the object. In other words, the forward solution is the process of computing the values of the 4N external variables represented by vector Y.

Equation 9 above represents the forward solution. Given any value choice of values for vector X (i.e., with one element set to 1 and all the other elements set to 0), Equation x defines the input-output relationship of light traveling through the object in terms of a 4N by 4N matrix: $CA^{-1}B - D$.

The entries of the $CA^{-1}B - D$ matrix depend on the quantities $w_{ij}f_{ij}$, $w_{ij}b_{ij}$ and $w_{ij}s_{ij}$. Equivalently, one can consider the quantities of interest to be $w_{ij}$, $f_{ij}$ and $b_{ij}$, because $s_{ij}$ is determined by the relation $$s_{ij} = \tfrac{1}{2}(1 - f_{ij} - b_{ij}) \quad \text{(Eq.10)}$$

for a two dimensional object and $$s_{ij} = \tfrac{1}{4}(1 - f_{ij} - b_{ij}) \quad \text{(Eq.11)}$$

for a three dimensional object.

In summary, for a two dimensional object there are $3N^2$ variables of the form $w_{ij}$, $f_{ij}$ and $b_{ij}$ which represent the light transmission characteristics of the object being imaged, and there are $16N^2$ equations relating these variables and given by entries of the 4N by 4N matrix $CA^{-1}B - D$.

Example of Forward Solution

The following is a detailed example of the exact equations for an object represented by a 2 by 2 set of voxels. This example is intended to show how all the elements of the matrices A, B, C and D are defined in terms of the $w_{ij}$, $f_{ij}$, $s_{ij}$ and $b_{ij}$ attenuation and scattering coefficients. The reason for using such a small example is so that all the elements of each matrix can be shown on a single page.

A 2 by 2 array of voxels has 16 ($4N^2$) equations defining the relationships between the external, internal and detector variables:

$$\rightarrow P_{11}^u = w_{11}$$
$$(f_{11}*P_{21}^u + b_{11}*P_{01}^d + s_{11}*P_{10}^r + s_{11}*P_{12}^l)$$

$$P_{11}^d = w_{11}(b_{11}*P_{21}^u + f_{11}*P_{01}^d + s_{11}*P_{10}^r + s_{11}*P_{12}^l)$$

$$P_{11}^r = w_{11}(s_{11}*P_{21}^u + s_{11}*P_{01}^d + f_{11}*P_{10}^r + b_{11}*P_{12}^l)$$

$$\rightarrow P_{11}^l = w_{11}$$
$$(s_{11}*P_{21}^u + s_{11}*P_{01}^d + b_{11}*P_{10}^r + f_{11}*P_{12}^l)$$

$$\rightarrow P_{12}^u = w_{12}$$
$$(f_{12}*P_{22}^u + b_{12}*P_{02}^d + s_{12}*P_{11}^r + s_{12}*P_{13}^l)$$

$$P_{12}^d = w_{12}(b_{12}*P_{22}^u + f_{12}*P_{02}^d + s_{12}*P_{11}^r + s_{12}*P_{13}^l)$$

$$\rightarrow P_{12}^r = w_{12}$$
$$(s_{12}*P_{22}^u + s_{12}*P_{02}^d + f_{12}*P_{11}^r + b_{12}*P_{13}^l)$$

$$P_{12}^l = w_{12}(s_{12}*P_{22}^u + s_{12}*P_{02}^d + b_{12}*P_{11}^r + f_{12}*P_{13}^l)$$

$$P_{21}^u = w_{11}(f_{21}*P_{31}^u + b_{21}*P_{11}^d + s_{21}P_{20}^r + s_{21}*P_{22}^l)$$

$$\rightarrow Phd\ 21^d = w_{11}$$
$$(b_{21}*P_{31}^u + f_{21}*P_{11}^d + s_{21}*P_{20}^r + s_{21}*P_{22}^l)$$

$$P_{21}^r = w_{11}(s_{21}*P_{31}^u + s_{21}*P_{11}^d + f_{21}*P_{20}^r + b_{21}*P_{22}^l)$$

$$\rightarrow P_{21}^l = w_{11}$$
$$(s_{21}*P_{31}^u + s_{21}*P_{11}^d + b_{21}*P_{20}^r + f_{21}*P_{22}^l)$$

$$P_{22}^u = w_{22}(f_{22}*P_{32}^u + b_{22}*P_{12}^d + s_{22}*P_{21}^r + s_{22}*P_{23}^l)$$

$$\rightarrow P_{22}^d = w_{22}$$
$$(b_{22}*P_{32}^u + f_{22}*P_{12}^d + s_{22}*P_{21}^r + s_{22}*P_{23}^l)$$

$$\rightarrow P_{22}^r = w_{22}$$
$$(s_{22}*P_{32}^u + s_{22}*P_{12}^d + f_{22}*P_{21}^r + b_{22}*P_{23}^l)$$

$$P_{22}^l = w_{22}(s_{22}*P_{32}^u + s_{22}*P_{12}^d + b_{22}*P_{21}^r + f_{22}*P_{23}^l) \quad \text{(Eq.12)}$$

The arrows above point to the eight equations involving external variables. The other eight equations involve internal variables. The eight detector variables are the variables $P_{ij}^*$ with indices of i or j equal to either 0 or 3.

In terms of the matrix equation above, and using the short hand notation $$F_{ij} = w_{ij}f_{ij}$$

$$B_{ij} = w_{ij}b_{ij}$$

$$S_{ij} = w_{ij}s_{ij}$$

X, Y, Z, A, B, C and D are defined as follows:

$$X = \begin{bmatrix} P_{01}^d \\ P_{02}^d \\ P_{13}^l \\ P_{23}^l \\ P_{32}^u \\ P_{31}^u \\ P_{20}^r \\ P_{10}^r \end{bmatrix} \quad Y = \begin{bmatrix} P_{11}^u \\ P_{12}^u \\ P_{12}^r \\ P_{22}^r \\ P_{22}^d \\ P_{21}^d \\ P_{21}^l \\ P_{11}^l \end{bmatrix} \quad Z = \begin{bmatrix} P_{12}^l \\ P_{11}^r \\ P_{12}^d \\ P_{22}^u \\ P_{22}^l \\ P_{21}^r \\ P_{21}^u \\ P_{11}^d \end{bmatrix}$$

$$C = - \begin{bmatrix} S_{11} & 0 & 0 & 0 & 0 & 0 & F_{11} & 0 \\ 0 & S_{12} & 0 & F_{12} & 0 & 0 & 0 & 0 \\ 0 & F_{12} & 0 & S_{12} & 0 & 0 & 0 & 0 \\ 0 & 0 & S_{22} & 0 & 0 & F_{22} & 0 & 0 \\ 0 & 0 & F_{22} & 0 & 0 & S_{22} & 0 & 0 \\ 0 & 0 & 0 & 0 & S_{21} & 0 & 0 & F_{21} \\ 0 & 0 & 0 & 0 & F_{21} & 0 & 0 & S_{21} \\ F_{11} & 0 & 0 & 0 & 0 & 0 & S_{11} & 0 \end{bmatrix}$$

$$D = - \begin{bmatrix} B_{11} & 0 & 0 & 0 & 0 & 0 & 0 & S_{11} \\ 0 & B_{12}S_{12} & 0 & 0 & 0 & 0 & 0 & 0 \\ 0 & S_{12}B_{12} & 0 & 0 & 0 & 0 & 0 & 0 \\ 0 & 0 & 0 & B_{22}S_{22} & 0 & 0 & 0 & 0 \\ 0 & 0 & 0 & S_{22}B_{22} & 0 & 0 & 0 & 0 \\ 0 & 0 & 0 & 0 & 0 & B_{21}S_{21} & 0 & 0 \\ 0 & 0 & 0 & 0 & 0 & S_{21}B_{21} & 0 & 0 \\ S_{11} & 0 & 0 & 0 & 0 & 0 & 0 & B_{11} \end{bmatrix}$$

$$A = - \begin{bmatrix} -1B_{12} & 0 & S_{12} & 0 & 0 & 0 & 0 \\ B_{11}-1 & 0 & 0 & 0 & 0 & S_{11} & 0 \\ 0 & S_{12}-1B_{12} & 0 & 0 & 0 & 0 & 0 \\ 0 & 0 & B_{22}-1 & 0 & S_{22} & 0 & 0 \\ 0 & 0 & S_{22} & 0 & -1B_{22} & 0 & 0 \\ 0 & 0 & 0 & 0 & B_{21}-1 & 0 & S_{21} \\ 0 & 0 & 0 & 0 & S_{21} & 0 & -1B_{21} \\ S_{11} & 0 & 0 & 0 & 0 & 0 & B_{11}-1 \end{bmatrix}$$

$$B = - \begin{bmatrix} 0 & S_{12}F_{12} & 0 & 0 & 0 & 0 & 0 & 0 \\ S_{11} & 0 & 0 & 0 & 0 & 0 & 0 & F_{11} \\ 0 & F_{12}S_{12} & 0 & 0 & 0 & 0 & 0 & 0 \\ 0 & 0 & 0 & S_{22}F_{22} & 0 & 0 & 0 & 0 \\ 0 & 0 & 0 & F_{22}S_{22} & 0 & 0 & 0 & 0 \\ 0 & 0 & 0 & 0 & 0 & S_{21}F_{21} & 0 & 0 \\ 0 & 0 & 0 & 0 & 0 & F_{21}S_{21} & 0 & 0 \\ F_{11} & 0 & 0 & 0 & 0 & 0 & 0 & S_{11} \end{bmatrix}$$

Note that the elements in the Y vector are the external variables corresponding to the voxels selected by going around the object's perimeter in a clockwise fashion, starting at position (1,1). The elements of the X vector are the detector variables for detectors selected by going around the detector array in a clockwise fashion, starting at position (0,1). The elements of the Z vector can be ordered in any arbitrary manner, but preferably with the variables for each voxel located close to one another.

The Inverse Solution

The "inverse solution" is a method of solving the following problem: given a set of light intensity measurements obtained by using an array of detectors as shown in FIG. 4, compute the $w_{ij}$, $f_{ij}$, $b_{ij}$ and $s_{ij}$ coefficients for all the voxels in the object being imaged. In other words, the inverse solution is the solution to the primary problem addressed by the present invention.

Figure 5:
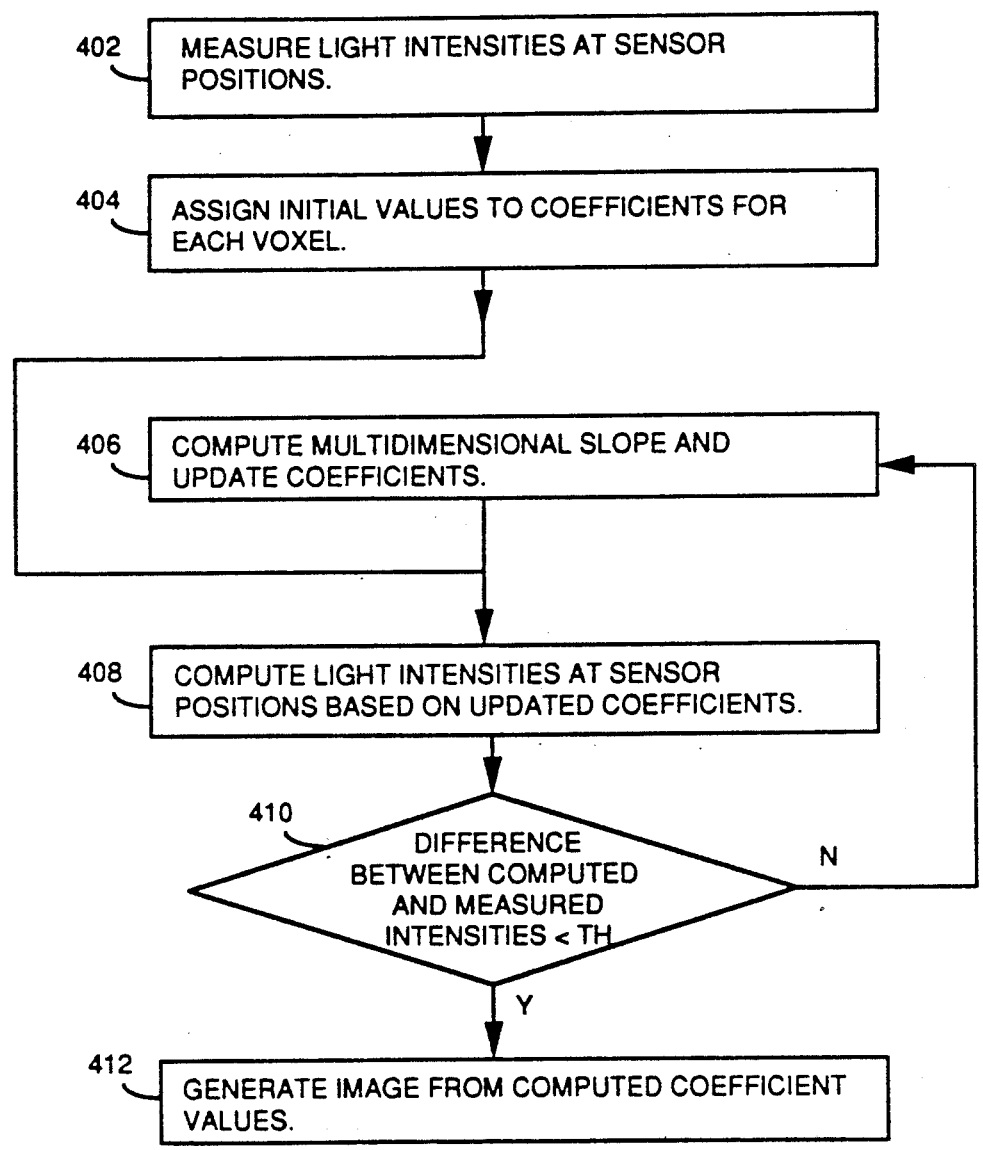
FIG. 5 is a flow chart of the imaging method used in the preferred embodiment of the invention.

Generally speaking, the inverse solution is an iterative process that works as follows. Referring to FIG. 5, one first takes the required measurements (box 402) and then makes an initial guess as to the values of the $w_{ij}$, $f_{ij}$, $b_{ij}$ and $s_{ij}$ coefficients for all the voxels in the object (box 404). If the initial guess is based on the expected structure inside the object, that may substantially improve the speed with which the inverse solution is computed. However, for the purposes of testing the first prototypes of the invention, the inventors have used an initial set of values corresponding to an object of uniform qualities, such as $w_{ij}=0.5$, $f_{ij}=0.7$, $b_{ij}=0.1$, and $s_{ij}=0.1$ for all voxels inside the object.

Next, given the current values of the attenuation and scattering coefficients, the imaging system computes the expected light intensities at each of the detectors positions (box 408). In other words, one uses the above described "forward solution" to compute how much light would emerge from the object at each detector position if the object's interior were accurately modelled by the current values of the attenuation and scattering coefficients.

Then, one determines the differences between the computed detector intensity values and those measured in step 402. These differences are then compared with a threshold to determine whether further computations are required (box 410). In the simplest embodiment, further computations are required if any of the differences (i.e., between any computed intensity value and the corresponding measurement) exceed a threshold value.

In the preferred embodiment, the parameter update module 134 (see FIG. 1 the differences are subjected to a requirement that the sum of the squares of the differences between the measured and computed values be less than a specified threshold value. More specifically, it first computes an error function, ERROR_FCN as follows:

$$\text{ERROR\_FCN} = \sum_{i=1}^{S} (\text{Measured Intensity at Sensor } i - \text{Computed Intensity at Sensor } i)^2 \quad \text{(Eq. 13)}$$

where S is the number of sensors at which measurements are taken. In the ideal case for a two dimensional system, S will be equal to 4N for an N by N array of voxels.

The parameter update module then computes a multi-dimensional slope or gradient of this error function (box 406). This multi-dimensional gradient is a vector, the components of which are the partial derivatives of the error function with respect to each of the parameter values:

$$\text{gradient} = (\text{grad}(p_1), \text{grad}(p_2), \ldots \text{grad}(p_{3N^2}))$$

$$\text{grad}(p_i) = \frac{\partial}{\partial p_i}(\text{ERROR\_FCN})$$

where ERROR_FCN is the error function and grad($p_i$) is the partial derivative of the error function with respect to parameter $p_i$. Note that the parameters here are the 3N coefficients $w_{ij}$, $f_{ij}$ and $b_{ij}$ described above. As is known to those skilled in the art of scientific computing, such partial derivatives can be numerically computed quite easily.

Next, the parameter updating module generates new values for the parameters (i.e., the attenuation and scattering coefficients) (box 406) by adjusting the current values of the parameters in a direction opposite to the gradient of the error function. That is, each individual parameter is adjusted in a way that is related to the multi-dimensional slope and the differences between the computed and measured intensity values:

$$p(x)_{i+1} = p(x)_i - f(\text{ERROR\_FCN}, \text{gradient}, x) \quad \text{(Eq.14)}$$

where $p(x)_i$ is the current value of one individual parameter, $p(x)_{i+1}$ is the adjusted value of that parameter, and f(ERROR_FCN,gradient,j) is a computed adjustment factor that is a function of the error function ERROR_FCN, the gradient of the error function ERROR_FCN, and the parameter p(x) that is being modified.

There are a number of well known numerical techniques for minimizing multidimensional (i.e., multivariable) functions, which we herein call "gradient descent" algorithms. See, for example, William H. Press, Brian P. Flannery, Saul A. Teukolsky, William T. Vetterling, *Numerical Recipes, The Art of Scientific Computing*, Cambridge University Press, sections 10.5 through 10.10, pp.294–334 (1976), which is hereby incorporated by reference. Any one of a number of such methods can be used with the present invention. The particular method used in preferred embodiment is a conjugate gradient method. Using this methodology, the values of the coefficients are changed so that the error function is minimized during most iterations. However, as will be understood by those skilled in the art, to prevent the process from getting stuck in local minima, the process occasionally allows a random move that may increase the value of the error function.

In summary, regardless of which gradient descent method is used, step 406 produces an updated set of coefficients that will better match the actual light propagation characteristics of the object being imaged.

Once the new coefficient values have been computed (box 406), the forward solution is recomputed as described above (box 408). Then the error function ERROR_FCN is computed once again, and its value is compared with a threshold value to determine if another iteration of the parameter updating process is required (box 410).

The iterative process represented by steps 406 through 410 continues until the value of the error function falls below the specified threshold—i.e., until the computed coefficients produce a forward solution that corresponds closely to the measured intensity values.

Finally, once the iterative computation process of steps 406 through 410 is completed, a series of images is generated from the computed coefficient values. For instance, the system will typically draw an image in which the darkness or color of each point corresponds to the attenuation coefficient $w_{ij}$ of the corresponding voxel, and another image in which the darkness or color of each point corresponds to the sideways scattering coefficient $s_{ij}$. Images based on the backwards and forward scattering coefficients $b_{ij}$ and $f_{ij}$ are also generated to depict different characteristics of the object.

Figure 6:
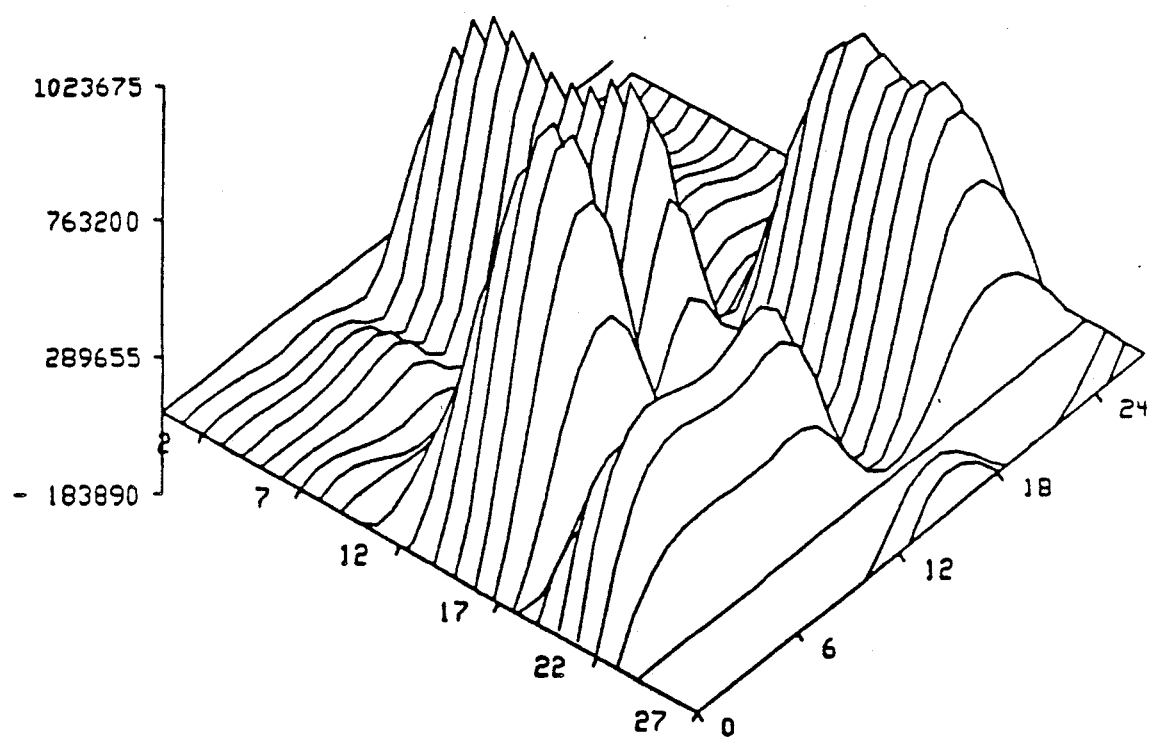
FIG. 6 depicts a map of the attenuation characteristics of an object.
Figure 7:
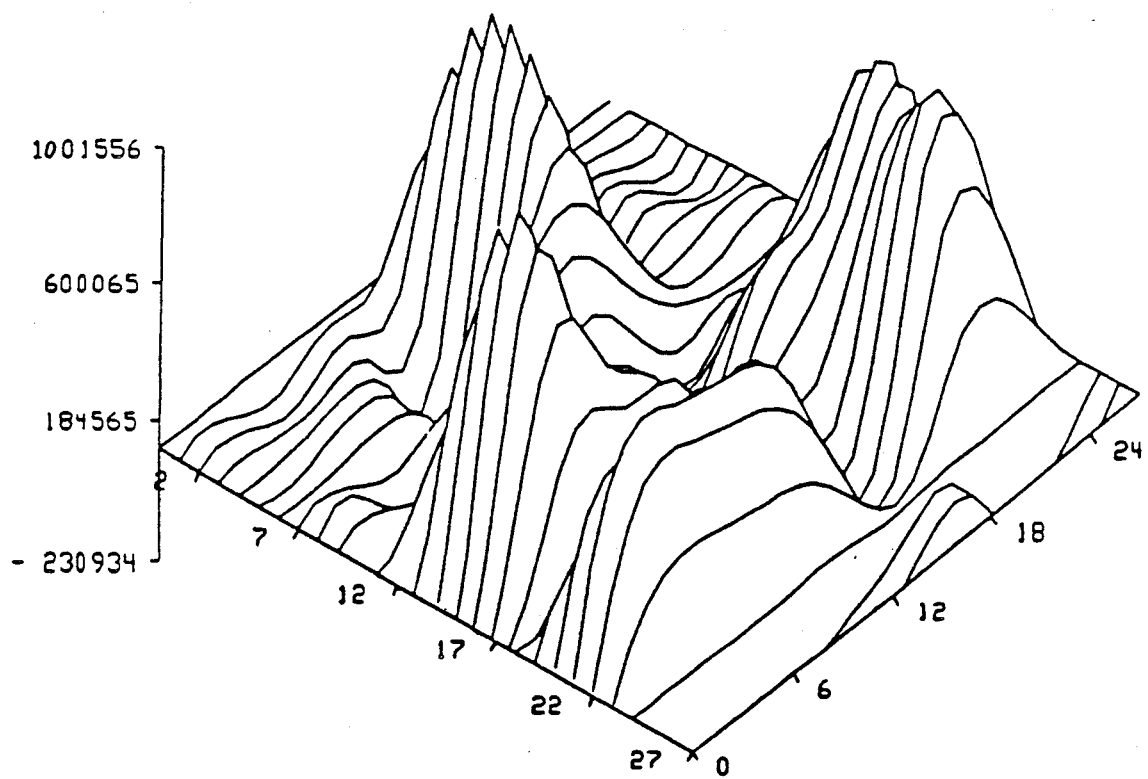
FIG. 7 depicts a map of a reconstruction of the object shown in FIG. 6 generated using a prototype of the present invention.

Referring to FIGS. 6 and 7, there is shown in FIG. 6 a map of the attenuation characteristics of an object (i.e., in a two dimensional slice through the object). Using a simulated prototype of the present invention, the attenuation characteristics of this object were reconstructed, resulting in the map shown in FIG. 7. More specifically, FIG. 7 is a map of the computed $V_{ij}$ coefficients (equal to $1 - w_{ij}$) for the object.

It is interesting to note that while the reconstructed image in FIG. 7 is generally quite accurate, the one portion of the object that is not as accurately reconstructed is a "dark region" located between two sections of high attenuation materials and towards the center of the object. This is to be expected, since once the light entering the object is highly attenuated, some or lost of the information regarding deeper regions of the object (i.e., behind the high attenuation regions) will be lost. It is believed by the inventors that a more accurate reconstruction would be obtained when using a three dimensional implementation of the invention. It is also expected that this problem regarding high attenuation regions may be overcome by using measurements based on two or more light frequencies that have distinct attenuation characteristics.

The image generation software 140 of the present invention generates additional images by mapping the computed $f_{ij}$, $b_{ij}$ and $s_{ij}$ coefficients. The method of mapping these coefficients into images is the same as for mapping the array of data values obtained when using CAT scan systems, magnetic resonance imaging systems, and so on. However, it is expected that the images based on the computed $f_{ij}$, $b_{ij}$ and $s_{ij}$ coefficients will provide information not available from CAT scan systems, which measure only the attenuation of x-rays by an object (corresponding to the $w_{ij}$ coefficient which is also computed by the present invention).

Figure 8A:
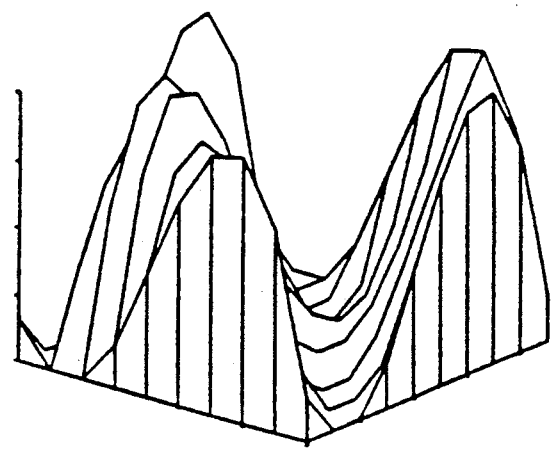
FIGS. 8A–8C depict a map of the forward scattering characteristics of a three dimensional object and two maps of reconstructions of the object with varying amounts of noise in the measurement signal.
Figure 9A:
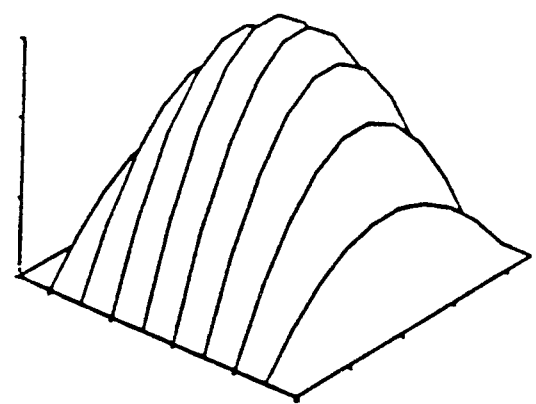
FIGS. 9A-9C depict a map of the attenuation characteristics of a three dimensional object and two maps of reconstructions of the object with varying amounts of noise in the measurement signal.
Figure 10A:
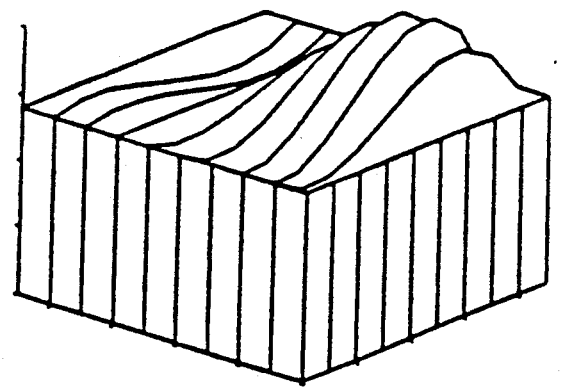
FIGS. 10A-10C depict a map of the side scattering characteristics of a three dimensional object and two maps of reconstructions of the object with varying amounts of noise in the measurement signal.

Next we show a set of images generated using a simulation of the invention with a three dimensional object modelled as a three dimensional array of voxels. FIG. 8A shows the attenuation characteristics of one slice (i.e., a two dimensional section) of this object, and FIGS. 9A and 10A show the forwards and side scattering characteristics of the object.

In these simulations, the measurements upon which the calculations are performed have been modified by adding different levels of multiplicative noise. More precisely, noise was added to the measurements as follows. Let $Mi_d, i_s$ denote a measurement by a detector at position $i_d$ when using a radiation source at position $i_s$. In other words, $Mi_d, i_s$ is the measurement value that would be obtained if there were no noise. Then we introduce a multiplicative noise of $\alpha\%$ as follows:

$$M(i_d, i_s) = M(i_d, i_s) * (1 + 0.01 * \alpha * X) \quad \text{(Eq.15)}$$

where $M(i_d, i_s)$ is the value of the measurement that would be obtained if there were no noise, X is a random variable taking values between 0 and 1, and M'($i_d$,$i_s$) the measurement value including noise.

Using two sets of modified measurement values, one set of measurement values representing a 1% noise factor and another set representing a 5% noise factor, the attenuation and scattering coefficients for the object were generated using the above described inverse solution technique.

Figure 8B:
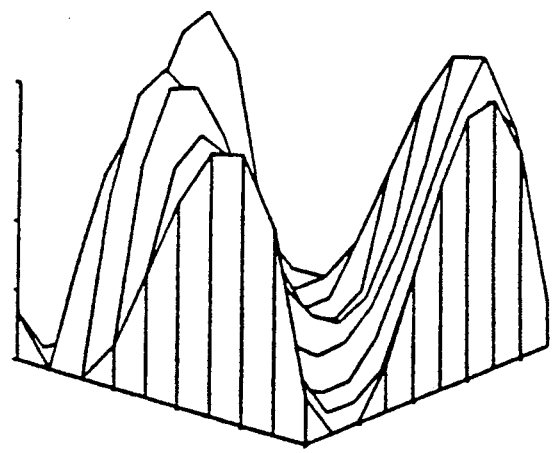
Figure 8C:
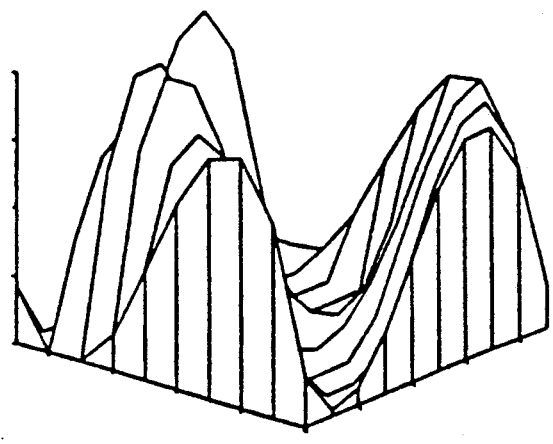
Figure 9B:
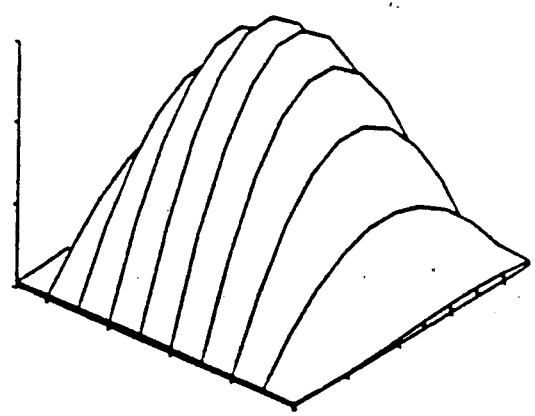
Figure 9C:
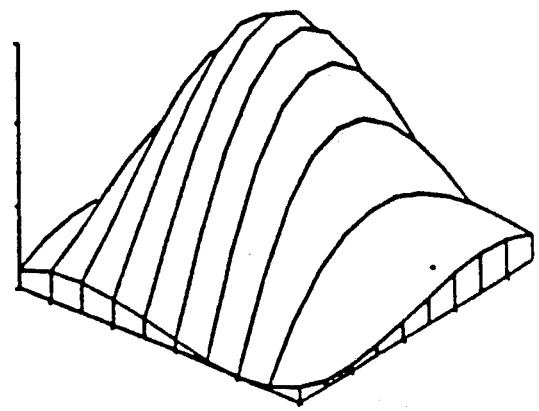
Figure 10B:
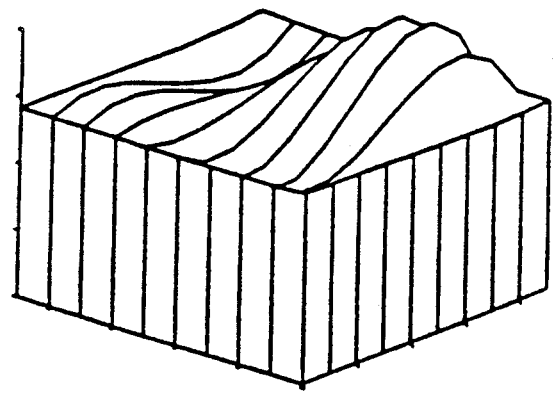
Figure 10C:
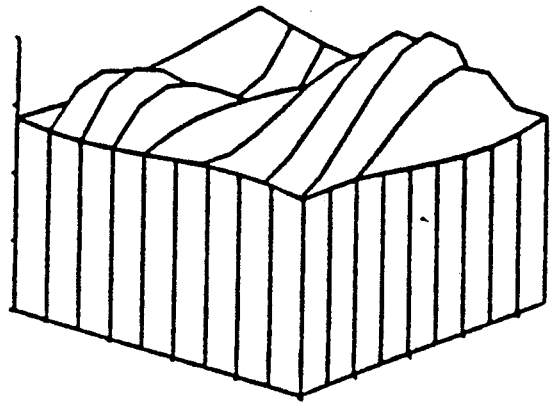

FIGS. 8B, 9B, and 10B represent the attenuation, forward scattering and side scattering characteristics of the reconstructed image when the measurement values include a 1% noise factor. FIGS. 8C, 9C, and 10C represent the attenuation, forward scattering and side scattering characteristics of the reconstructed image when the measurement values include a 5% noise factor. As can be seen, while the reconstructed images generated are affected by noise, the general characteristics of the object are still reconstructed quite well with a 5% noise factor.

While the present invention has been described with reference to a few specific embodiments, the description is illustrative of the invention and is not to be construed as limiting the invention. Various modifications may occur to those skilled in the art without departing from the true spirit and scope of the invention as defined by the appended claims.

What is claimed is:

1. A system for generating images corresponding to the internal characteristics of an object, comprising:
   radiating means for generating a directed beam of radiation, said beam being directed at distinct times at each of a multiplicity of input positions around an object;
   sensor means arrayed around at least a portion of said object for measuring the intensity of radiation emerging from said object at a multiplicity of sensor positions;
   data storage means, coupled to said sensor means, for storing a multiplicity of sets of measured intensity values, each set of intensity values corresponding to the intensities of radiation measured by said sensor means while said radiating means is generating a beam directed at distinct ones of said input positions;
   reconstruction means, coupled to said data storage means, for reconstructing a composite image of a portion of the interior of said object, said reconstructing means computing, using said stored intensity values, an array of image data values comprising radiation attenuation and radiation scattering coefficients which characterize both radiation attenuation and scattering characteristics of said portion of the interior of said object.

2. The imaging system of claim 1, wherein said reconstruction means includes means for repeatedly (A) computing intensity values comprising the intensity of radiation that would emerge from said object at said sensor positions while said object is radiated at at least selected ones of said input positions, were said object characterized by said computed attenuation and scattering coefficients, (B) evaluating differences between said computed and measured intensity values, and (C) adjusting said computed attenuation and scattering coefficients, until the difference between said computed and measured intensity values meet predefined criteria.

3. A method of imaging the interior of an object, the steps of the method comprising:
   generating a directed beam of radiation, said beam being directed at distinct times at each of a multiplicity of input positions around an object;
   measuring the intensity of radiation emerging from said object at a multiplicity of sensor positions;
   reconstructing a composite image of a portion of the interior of said object, including computing, using said measured intensity values, an array of image data values comprising radiation attenuation and radiation scattering coefficients which characterize both radiation attenuation and scattering characteristics of said portion of the interior of said object.

4. The imaging method of claim 3, wherein said reconstructing step repeatedly (A) computing intensity values comprising the intensity of radiation that would emerge from said object at said sensor positions while said object is radiated at at least selected ones of said input positions, were said object characterized by said computed attenuation and scattering coefficients, (B) evaluating differences between said computed and measured intensity values, and (C) adjusting said computed attenuation and scattering coefficients, until the differences between said computed and measured intensity values meet predefined criteria.

5. A system for generating images corresponding to the internal characteristics of an object, comprising:
   radiating means for generating a directed beam of radiation, said beam being directed at distinct times at each of a multiplicity of input positions around an object;
   sensor means arrayed around at least a portion of said object for measuring the intensity of radiation emerging from said object at a multiplicity of sensor positions;
   data storage means, coupled to said sensor means, for storing a multiplicity of sets of measured intensity values, each set of intensity values corresponding to the intensities of radiation measured by said sensor means while said radiating means is generating a beam directed at distinct ones of said input positions;
   reconstruction means, coupled to said data storage means, for reconstructing a composite image of at least a portion of the interior of said object, said reconstructing means including:
   (A) modeling means for modeling the interior of said object as an array of voxels, each voxel being characterized by an attenuation coefficient and a plurality of scattering coefficients, said coefficients corresponding to portions of radiation entering said voxel which are absorbed and scattered by said voxel;
   said modeling means including:
   coefficient denoting means for denoting current values for said attenuation and scattering coefficients for all of said voxels in said model of the interior of said object, including means for assigning initial values to said coefficients;
   forward computing means for computing a set of intensity values comprising the intensity of radiation that would emerge from said object at said sensor positions while said object is radiated at at least selected ones of said input positions, were said object characterized by said current values for said attenuation and scattering coefficients as denoted by said coefficient denoting means; and
   updating means, coupled to said forward computing means, said data storage means and said coefficient denoting means, for evaluating differences between said computed and measured intensity values, and for generating new values for said attenuation and scattering coefficients which reduce the differences between said computed and measured intensity values; and (B) control means, coupled to said forward computing and updating means, including means for performing a successive approximation process in which said forward computing and updating means repeatedly compute intensity values and then update said attenuation and scattering coefficients until the differences between said computed and measured intensity values meet predefined criteria.

6. An imaging system as set forth in claim 5, said reconstruction means including image generation means for generating an image corresponding to at least a subset of said attenuation and scattering coefficients.

7. An imaging system as set forth in claim 5, said updating means including:
gradient means for computing a predefined function of said differences between said computed and measured intensity values and for computing a multi-dimensional slope corresponding to partial differentials of said predefined function with respect to each of said coefficients;
means for generating new values for said coefficients by adjusting the current values of said coefficients by amounts corresponding to said multi-dimensional slope.

8. An imaging system as set forth in claim 5, said updating means including:
gradient means for computing a predefined function corresponding to the sum of the squares of said differences between said computed and measured intensity values, and for computing a multi-dimensional slope corresponding to partial differentials of said predefined function with respect to each of said coefficients;
means for generating new values for said coefficients by adjusting the current values of said coefficients by amounts corresponding to said multi-dimensional slope.

9. A system for generating images corresponding to the internal characteristics of an object, comprising:
light generating means for generating a directed beam of light, said beam being directed at distinct times at each of a multiplicity of input positions around an object;
sensor means arrayed around at least a portion of said object for measuring the intensity of light emerging from said object at a multiplicity of sensor positions;
data storage means, coupled to said sensor means, for storing a multiplicity of sets of measured intensity values, each set of intensity values corresponding to the intensities of light measured by said sensor means while said light generating means is generating a beam directed at distinct one of said input positions;
reconstruction means, coupled to said data storage means, for reconstructing a composite image of at least a portion of the interior of said object, said reconstructing means including:
(A) modeling means for modeling the interior of said object as an array of voxels, each voxel being characterized by an attenuation coefficient and a plurality of scattering coefficients, said coefficients corresponding to portions of light entering said voxel which are absorbed and scattered by said voxel;
said modeling means including:
coefficient denoting means for denoting current values for said attenuation and scattering coefficients for all of said voxels in said model of the interior of said object, including means for assigning initial values to said coefficients;
forward computing means for computing a set of intensity values comprising the intensity of radiation that would emerge from said object at said sensor positions while said object is radiated with light at at least selected ones of said input positions, were said object characterized by said current values for said attenuation and scattering coefficients as denoted by said coefficient denoting means; and
updating means, coupled to said forward computing means, said data storage means and said coefficient denoting means, for evaluating differences between said computed and measured intensity values, and for generating new values for said attenuation and scattering coefficients which reduce the differences between said computed and measured intensity values; and (B) control means, coupled to said forward computing and updating means, including means for performing a successive approximation process in which said forward computing and updating means repeatedly compute intensity values and then update said attenuation and scattering coefficients until the differences between said computed and measured intensity values meet predefined criteria.

10. An imaging system as set forth in claim 9, said reconstruction means including image generation means for generating an image corresponding to at least a subset of said transmission, reflection and scattering coefficients.

11. An imaging system as set forth in claim 9, said updating means including:
gradient means for computing a predefined function of said differences between said computed and measured intensity values and for computing a multi-dimensional slope corresponding to partial differentials of said predefined function with respect to each of said coefficients;
means for generating new values for said coefficients by adjusting the current values of said coefficients by amounts corresponding to said multi-dimensional slope.

12. An imaging system as set forth in claim 9, said updating means including:
gradient means for computing a predefined function corresponding to the sum of the squares of said differences between said computed and measured intensity values, and for computing a multi-dimensional slope corresponding to partial differentials of said predefined function with respect to each of said coefficients;
means for generating new values for said coefficients by adjusting the current values of said coefficients by amounts corresponding to said multi-dimensional slope.

13. A method of imaging the interior of an object, the steps of the method comprising:

generating a directed beam of radiation directed at distinct times at each of a multiplicity of input positions around an object;

measuring the intensity of radiation emerging from said object at a multiplicity of sensor positions and storing sets of measured intensity values, each set of intensity values corresponding to said measured intensities while said object is being radiated by a beam directed at distinct ones of said input positions;

reconstructing a composite image of at least a portion of the interior of said object, said reconstructing step including:

(A) modeling the interior of said object as an array of voxels, each voxel being characterized by an attenuation coefficient and a plurality of scattering coefficients, said coefficients corresponding to portions of radiation entering said voxel which are absorbed and scattered by said voxel; said modeling step including the steps of:

denoting current values for said attenuation and scattering coefficients for all of said voxels;

computing a set of intensity values comprising the intensity of radiation that would emerge from said object at said sensor positions while said object is radiated at at least selected ones of said input positions, were said object characterized by said current values for said attenuation and scattering coefficients;

evaluating differences between said computed and measured intensity values, and updating said current values of said coefficients by computing new values for said attenuation and scattering coefficients which reduce the differences between said computed and measured intensity values; and (B) performing a successive approximation process by repeatedly performing said computing, evaluating and updating steps until the differences between said computed and measured intensity values meet predefined criteria.

14. A method of imaging the interior of an object as set forth in claim 13, said reconstructing step including generating an image corresponding to at least a subset of said attenuation and scattering coefficients.

15. A method of imaging the interior of an object as set forth in claim 10, said updating step including the steps of:

computing a predefined function of the differences between said computed and measured intensity values, computing a multi-dimensional slope corresponding to partial differentials of said predefined function with respect to each of said coefficients; and computing new values for said coefficients by adjusting the current values of said coefficients by amounts corresponding to said multi-dimensional slope.

16. A method of imaging the interior of an object as set forth in claim 19, said updating step including the steps of:

computing a predefined function corresponding to the sum of the squares of the differences between said computed and measured intensity values;

computing a multi-dimensional slope corresponding to partial differentials of said predefined function with respect to each of said coefficients; and computing new values for said coefficients by adjusting the current values of said coefficients by amounts corresponding to said multi-dimensional slope.

* * * * *